United States Patent
Winsor

(10) Patent No.: US 9,987,477 B2
(45) Date of Patent: Jun. 5, 2018

(54) SPLIT SEPTUM ASSEMBLY FOR AN INTRAVENOUS INJECTION SITE

(71) Applicant: Nexus Medical, LLC, Lenexa, KS (US)

(72) Inventor: Chris Winsor, Overland Park, KS (US)

(73) Assignee: Nexus Medical, LLC, Lenexa, KS (US)

( * ) Notice: Subject to any disclaimer, the term of this patent is extended or adjusted under 35 U.S.C. 154(b) by 699 days.

(21) Appl. No.: 14/613,561

(22) Filed: Feb. 4, 2015

(65) Prior Publication Data

US 2015/0224296 A1     Aug. 13, 2015

Related U.S. Application Data

(60) Provisional application No. 61/937,804, filed on Feb. 10, 2014.

(51) Int. Cl.
*A61M 39/04* (2006.01)
*A61M 39/00* (2006.01)
*A61M 39/02* (2006.01)

(52) U.S. Cl.
CPC ... *A61M 39/045* (2013.01); *A61M 2039/0063* (2013.01); *A61M 2039/0072* (2013.01); *A61M 2039/0205* (2013.01)

(58) Field of Classification Search
CPC .. A61M 2039/1072; A61M 2039/0063; A61M 2039/0072; A61M 2039/0205;

(Continued)

(56) References Cited

U.S. PATENT DOCUMENTS

2002/0147431 A1* 10/2002 Lopez ............... A61M 39/045
                                                          604/256
2007/0225648 A1    9/2007 Winsor et al.
(Continued)

FOREIGN PATENT DOCUMENTS

WO       98/26835      6/1998
WO    2008/057956 A2   5/2008

OTHER PUBLICATIONS

European Search Report dated Nov. 26, 2015, in European Patent Application No. 15154060.6, Applicant: Nexus Medical, LLC.

*Primary Examiner* — Nathan R Price
*Assistant Examiner* — Justin L Zamory
(74) *Attorney, Agent, or Firm* — Erise IP, P.A.

(57) ABSTRACT

An intravenous injection site having a split septum assembly interfit with the site for the intravenous administration of fluids to a patient. The split septum assembly has a resilient and compressible split septum having an axially-formed slit for receipt of a blunt cannula, needle, or other medical device through said slit, a septum holder for receipt of the split septum, and a septum housing for receipt of the combined septum holder and split septum. The septum includes a body and a flange extending radially from the body. A projection extends from the flange. The septum is mounted within the septum holder, and the septum holder is mounted within the septum housing to provide axial compression of the flange. This axial compression presents a double hermetic seal that significantly minimizes or prevents proximal leakage of fluid through the slit or around the septum holder when the cannula is removed.

22 Claims, 8 Drawing Sheets

(58) Field of Classification Search
CPC ...... A61M 2039/066; A61M 2039/064; A61M 2039/2426; A61M 2039/027; A61M 2025/0035
See application file for complete search history.

(56) References Cited

U.S. PATENT DOCUMENTS

2008/0215004 A1* 9/2008 Harding .............. A61M 39/045
 604/122
2010/0030163 A1* 2/2010 Carrez ................. A61M 39/22
 604/256

* cited by examiner

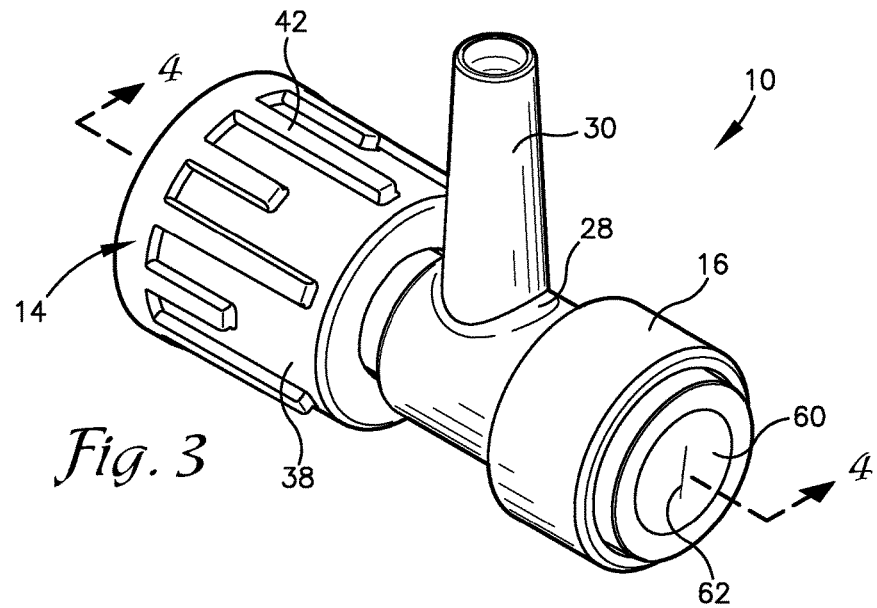
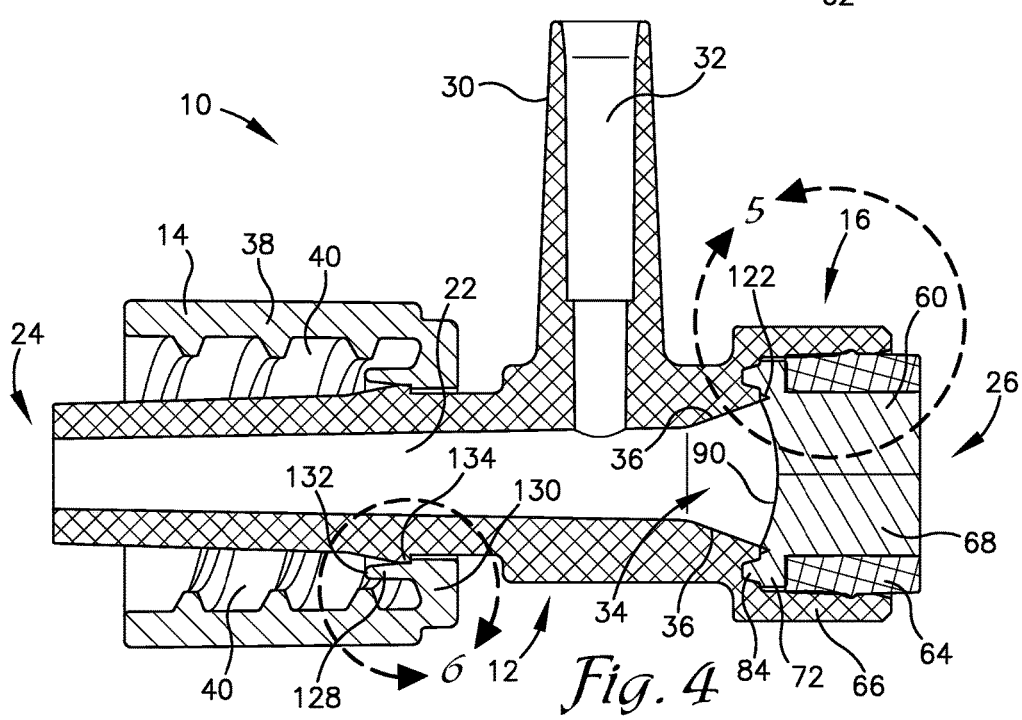

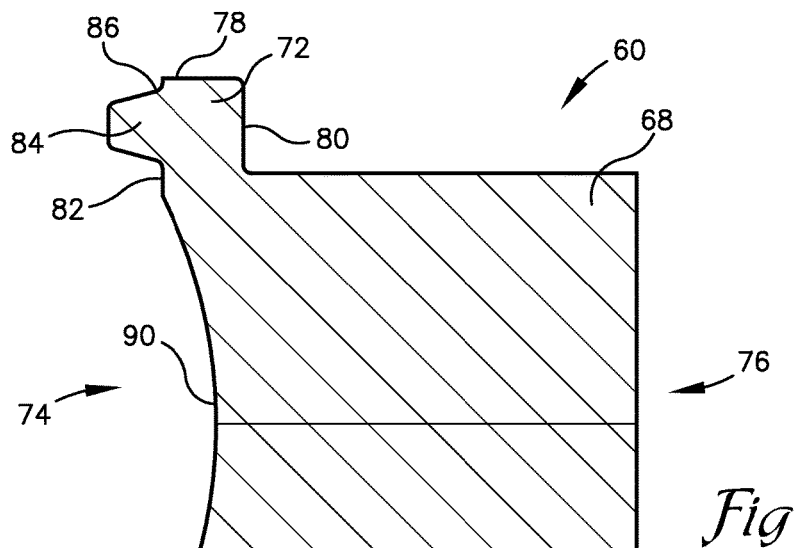
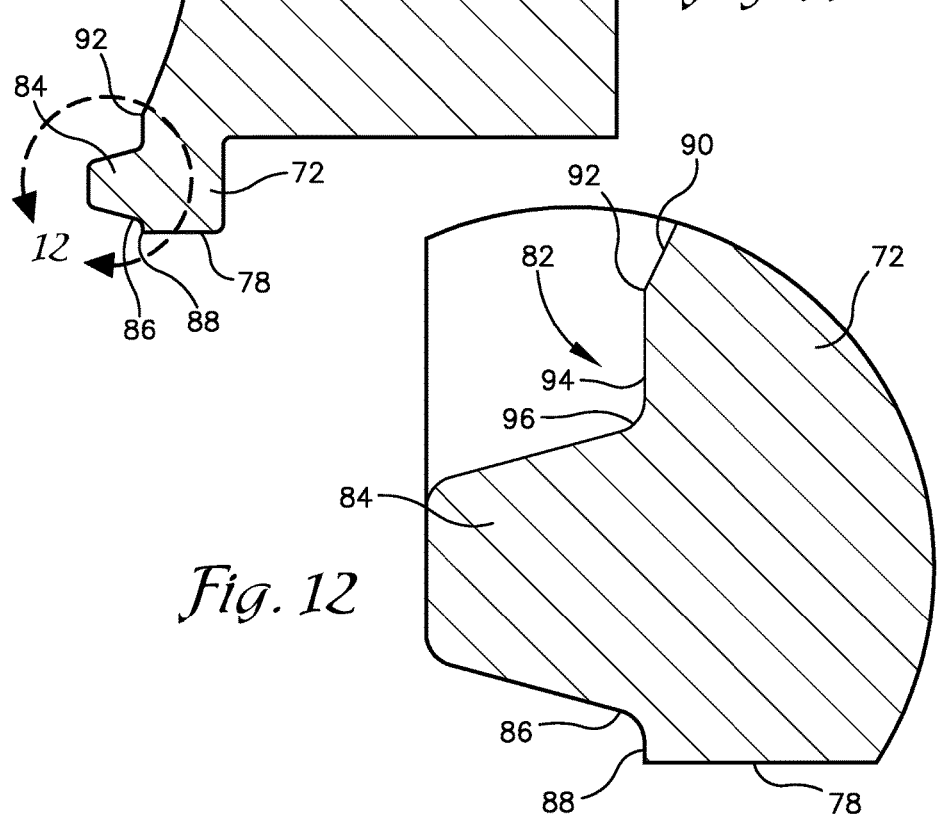

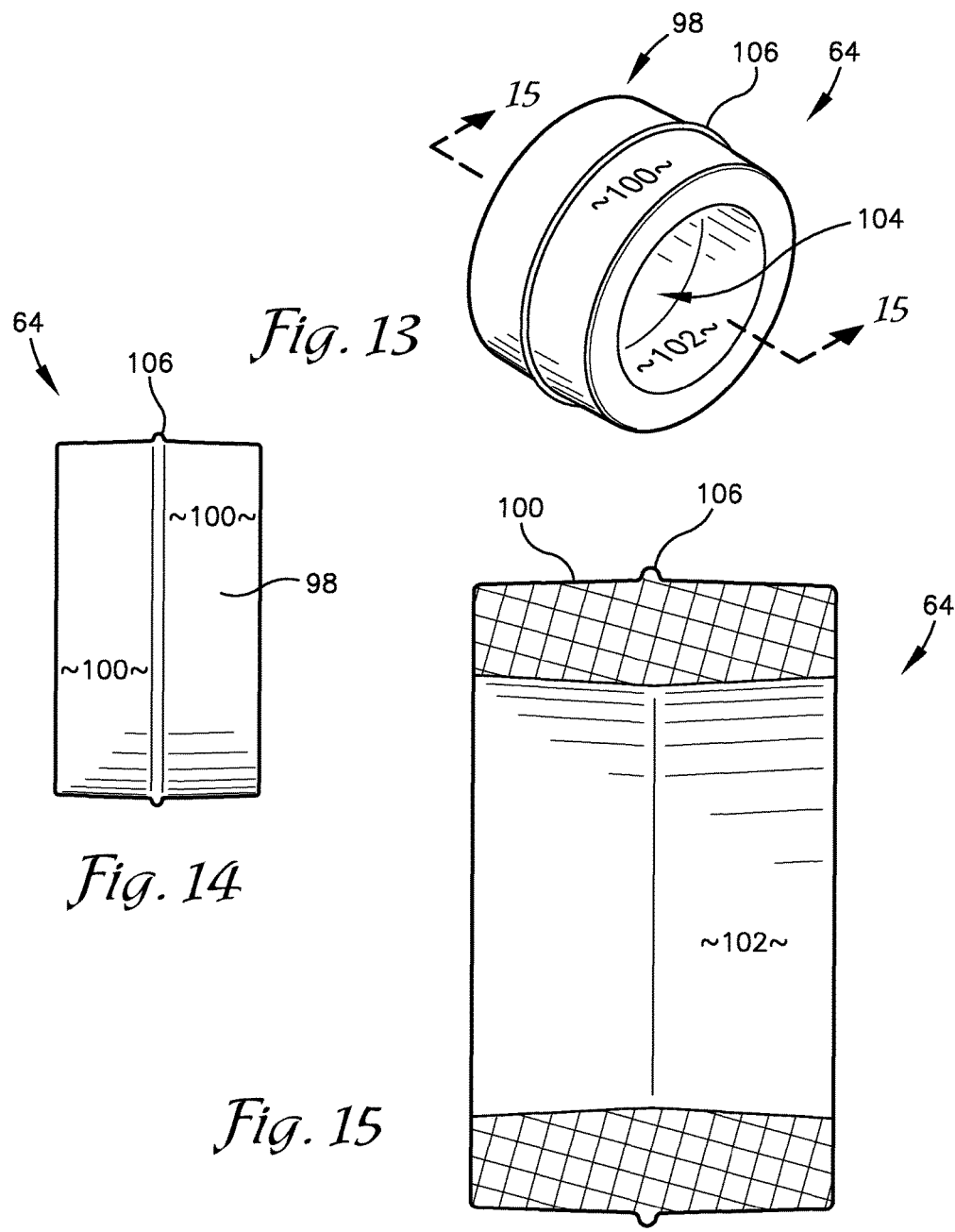

SPLIT SEPTUM ASSEMBLY FOR AN INTRAVENOUS INJECTION SITE

RELATED APPLICATION

The present non-provisional application claims priority benefit, with regard to all common subject matter, of U.S. Provisional Application No. 61/937,804, filed Feb. 10, 2014, and entitled "SPLIT SEPTUM ASSEMBLY FOR AN INTRAVENOUS INJECTION SITE" (the '804 Provisional Application). The '804 Provisional Application is hereby incorporated by reference in its entirety.

BACKGROUND

1. Field

Embodiments of the invention relate to intravenous injection sites for the administration of fluids to a patient. More particularly, embodiments are directed to an intravenous injection site having a split septum assembly in fluid communication and interfit with the site.

2. Related Art

Intravenous devices are used to administer medicaments and other parenteral fluids to patients. The devices include an injection site having a fluid passageway. A distal end of the casing near the patient is coupled with a catheter, needle, or other medical device inserted into the patient. A cannula (metal or plastic) or needle is coupled with a proximal end of the casing near the clinician. A septum is provided at the proximal end of the casing to receive the cannula or needle. The septum assists in preventing fluid flow, including blood reflux, into and out of the casing. Blood reflux potentially leads to clotting of the blood and occlusion of the injection site.

Such intravenous devices present several problems. In a first problem, a fluid passageway fluid connected to the septum is generally axially straight, especially proximate the septum. When the clinician inserts the cannula or needle through the septum, fluid from the cannula or needle is inserted into the fluid passageway. However, because of the generally straight-sided fluid passageway, the clinician must insert the cannula or needle at a general center point of the septum. If the clinician is off-axis in inserting the cannula or needle, i.e., if the clinician does not center a tip of the cannula or needle in the septum, then the cannula or needle may impinge on the fluid passageway walls. This causes the clinician to retract the cannula or needle and reinsert. This retraction of the cannula or needle is undesirable, as it can introduce bacteria into the septum.

A second problem is a size of the form factor of intravenous devices. The form factor, i.e., a general shape and size of the housing of the intravenous device, is usually approximately 27.55 mm (1.08 in) along its axial length, and approximately 9.96 mm (0.39 in) along its transverse width at its widest point. This is a relatively large overall size of the form factor for use with neonates or animals, such as cats and dogs, that have small bones. However, simply making a smaller form factor with the same general structure as standard-sized form factors presents new problems. As the form factor becomes smaller, and consequently the septum and surrounding housing becomes smaller, it becomes more difficult for the septum to seal against undesired fluid flow, especially with use of the larger-diameter cannula (as compared to the needle). Another issue with making the form factor smaller is that the priming volume is reduced.

SUMMARY

Embodiments of the invention relate to a miniaturized intravenous injection site for use with animals or humans, especially neonates. The intravenous injection side has a split septum assembly interfit with the site. The split septum assembly includes a resilient and compressible split septum for receiving a blunt cannula or needle through a slit formed in the septum. In embodiments, the split septum assembly has an axial length extending along an axis of a fluid passageway of the intravenous injection site when the split septum assembly is coupled with the site, a transverse width, a distal end oriented towards a patient when the split septum assembly is coupled with the intravenous injection site, and a proximal end oriented towards a clinician administering fluids to the patient. The split septum assembly broadly comprises a resilient and compressible split septum having an axially-formed slit for receipt of a blunt cannula, needle, or other medical device through said slit, a septum holder for receipt of the split septum, and a septum housing for receipt of the combined septum holder and split septum.

The septum includes a generally cylindrical body presenting a radial-most outer surface that has an outer diameter, and an annular flange circumscribing the radial-most outer surface of the septum body at a distal end of the septum body. The flange extends radially from the body of the septum to present a radial-most outer edge of the flange having an outer diameter of the flange. The outer diameter of the flange is greater than the outer diameter of the septum body, and an axial length of the septum body is greater than an axial length of the flange. The flange includes a distally-extending locating and sealing projection annularly formed on the flange. The flange is axially compressed when in use, such that the flange and corresponding projection present a double hermetic seal to prevent proximal leakage of fluids through the septum or around the septum holder.

The septum holder has a generally cylindrically shaped body presenting a radial-most outer surface having an outer diameter and a radial-most inner surface having an inner diameter. The septum holder includes an annular locking ring formed on the radial-most outer surface of the septum holder body and circumscribing the body. When the split septum body is positioned within the septum holder, the split septum flange extends beyond a transverse periphery of the septum holder.

The septum housing has a proximal end that is open for positioning of the combined septum holder and split septum therethrough, and a distal end that is open to the fluid passageway of the injection site. The septum housing further has a generally cylindrically shaped body having a radial-most outer surface and a radial-most inner surface presenting an inner diameter, a distally-extending annular locating groove for receipt of the locating and sealing projection on the flange of the septum, and a radially-extending annular locking groove for interconnecting with the locking ring formed on the septum holder.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 3 is a perspective view of the injection site of FIG. 1 and including a rotating locking collar secured on a portion of the injection site;

FIG. 4 is a vertical cross-sectional view through line 4-4 of FIG. 3;

FIG. 11 is a horizontal cross-sectional view through line 11-11 of FIG. 9;

FIG. 12 is a magnified view of a portion of the septum as indicated in detail 12 of FIG. 11;

FIG. 13 is a proximal perspective view of a septum holder of embodiments of the invention;

FIG. 14 is a side view of the septum holder of FIG. 13;

FIG. 15 is a vertical cross-sectional view through line 15-15 of FIG. 13; and

Figure 1:
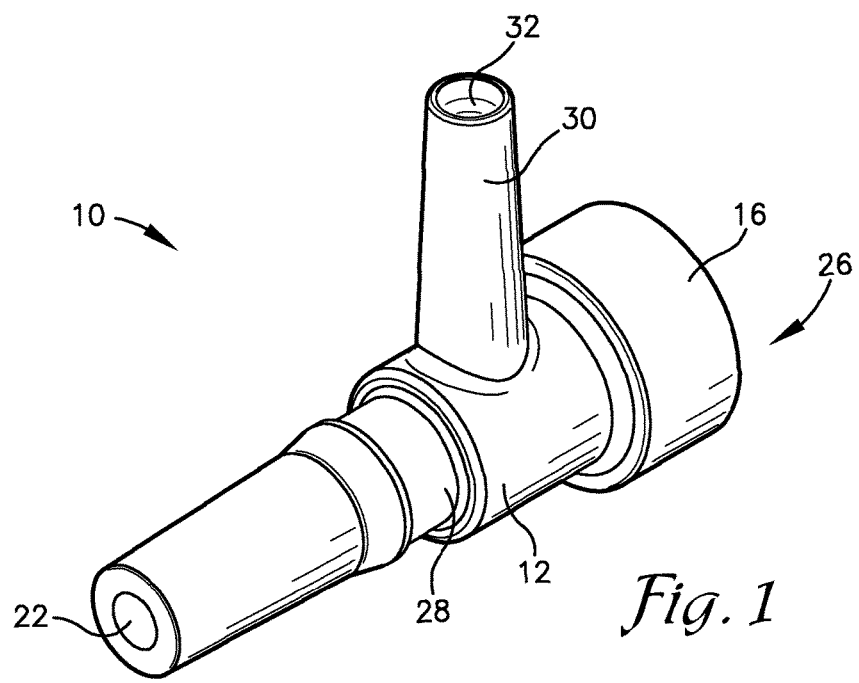
FIG. 1 is a first perspective view of an injection site for receipt of a septum of embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the present technology can include a variety of combinations and/or integrations of the embodiments described herein.

Figure 7:
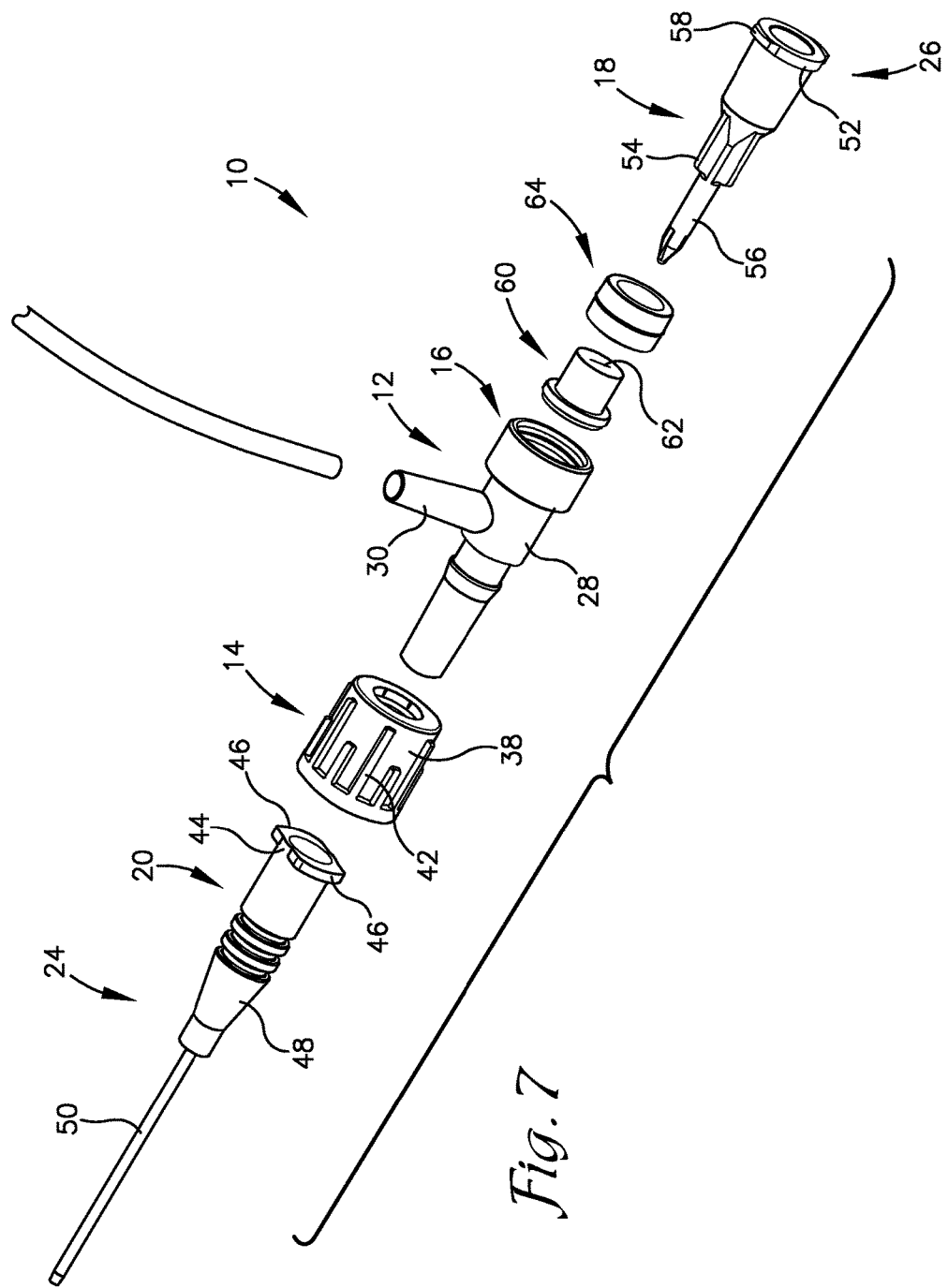
FIG. 7 is an exploded view of the various components of the injection site.

Turning now to the drawings and particularly FIG. 7, the intravenous injection site 10 broadly comprises a luer body 12, a rotating threaded collar 14, and a split septum assembly 16. A cannula 18 or a needle may be inserted into the split septum assembly 16 for the administration of fluids, such as parenteral fluids or medicaments, to a patient. The rotating threaded collar 14 may be removably coupled with a catheter 20 intravenously inserted into the patient. In embodiments, the patient may be a human or an animal. Although the injection site 10 is described and illustrated with the catheter 20, the site 10 can also be used in other applications (e.g., with other types of connection components, tubing, etc.). A form factor of the intravenous injection site 10, i.e., a size and a shape of the luer body 12 and the split septum assembly 16, is miniaturized relative to standardized injection sites. The form factor operates particularly well with patients such as neonates and small animals. In embodiments of the invention, the intravenous injection site has an axial length of approximately less than 30.5 mm (1.2 inches), approximately less than 25.4 mm (1 inch), or approximately 24.6 mm (0.97 inch) or 24.9 mm (0.98 inch); and a transverse width at its widest point of approximately less than 12.7 mm (0.5 inch), approximately less than 10.1 mm (0.4 inch), or approximately 8.3 mm (0.33 inch) or 8.6 mm (0.34 inch).

Reference will be made herein to various orientations and dimensions of the injection site 10 and its components. As used herein, the injection site 10 and its components have axial lengths that extend in a direction of a fluid passageway 22 (see, FIG. 4), as described below. The injection site 10 and components also present a transverse width that is generally perpendicular to an axis of the fluid passageway 22. A distal end 24 of the injection site 10 and components is the end oriented towards a patient when the injection site is in use by a clinician (i.e., the end towards the catheter 20), and a proximal end 26 of the injection site 10 and components is the end oriented towards a clinician administering fluids to the patient (i.e., the end towards the split septum assembly 16). Many of the injection site 10 components are generally cylindrical to present a radius from the axis of the fluid passageway 22 and to an outermost radial surface of the component when the injection site 10 is viewed from either its proximal or distal end or otherwise viewed in a horizontal cross section. Therefore, reference to a "radial-most" surface refers to the surface that is bounded by the radius extending between the passageway axis and the particular surface. For clarity, the passageway axis generally bisects the fluid passageway 22.

Referring now to FIGS. 1-4, in embodiments of the invention the luer body 12 is a slip luer T-site body comprising an elongated primary body portion 28 having the fluid passageway 22 formed therethrough, such that the fluid passageway 22 is a primary fluid passageway. Reference to "fluid passageway" or "fluid passageway 22" herein should be understood to include "primary fluid passageway" through the primary body portion 28 of the luer body 12. A secondary body portion 30 extends generally perpendicularly from the primary body portion 28 and presents a secondary fluid passageway 32 (see, FIG. 4). The luer body 12 is in embodiments formed of a molded rigid thermoplastic resin (MAKROLON® by BAYER®). The primary and secondary body portions 28,30 of the luer body 12 are integrally formed to present a unitary, monolithic structure. However, in embodiments, the secondary body portion 30 may be removably coupled to the primary body portion 28, such as via threaded connectors (not shown).

The secondary body portion 30 provides a secondary access point for the administration of fluids to the patient and via the secondary fluid passageway 32. As shown in FIG. 4, the secondary fluid passageway 32 intersects the primary fluid passageway 22, such that fluids administered via the secondary body portion 30 flow to the primary fluid passageway 22. In use, the primary fluid passageway 22 is fluidly connected to the catheter 20 for administration of fluids intravenously, as discussed in more detail below.

The primary fluid passageway 22 extends the axial length, or almost the entire axial length, of the primary body portion 28 of the luer body 12. The luer body 12 thus presents an axial length and proximal and distal ends. The rotating threaded collar 14 is coupled to the distal end 24 of the luer body 12, and the split septum assembly 16 is either integrally formed with or coupled to the proximal end 26 of the luer body 12, as described in more detail below. As shown in FIG. 4, the primary fluid passageway 22 is an elongated opening formed through the primary body portion 28 of the luer body 12. A proximal segment 34 of the primary fluid passageway 22 is generally conical in shape, such that a width of the primary fluid passageway 22 tapers, i.e., narrows, from a proximal-most end of the fluid passageway 22 and towards a distal direction. That is, the conically-shaped proximal segment 34 presents fluid passageway walls 36 that are inwardly-angled in a distal direction. In embodiments, the angle of the conically-shaped proximal segment 34 is approximately 20-60 degrees, approximately 30-50 degrees, or is approximately 40 degrees. The conically-shaped proximal segment 34 assists in the location of a needle within the fluid passageway 22. In particular, it is common for a clinician inserting a needle through the septum (as described below) to insert the needle at an angle relative to a transverse plane of the split septum assembly 16. When this occurs in a primary fluid passageway that is generally straight-sided at its proximal end, the needle will impinge the fluid passageway wall, which requires the clinician to pull the needle proximally out and reinsert. This potentially introduces particulate into the fluid passageway and generally impacts the ease of administering fluids. Thus, the conically-shaped segment 34 of the fluid passageway 22 of embodiments of the invention allows room for a tip of the needle inserted at an angle relative to the transverse plane of the split septum assembly 16 to be guided into the fluid passageway 22 in a straighter orientation.

Turning now to FIGS. 3-4, the rotating threaded collar 14 includes an outer body 38 and a plurality of internal threads 40 for rotatably coupling the collar 14 to the distal end 24 of the primary body portion 28 of the luer body 12. The outer body 38 of the collar 14 may include a plurality of gripping protrusions 42 to allow the clinician to interconnect the collar 14 with the luer body 12. The plurality of internal threads 40 may be rotated onto the luer body 12, as best illustrated in FIG. 4. The collar 14 may include various anti-rotation features, which are discussed in more detail below.

As noted above, the rotating collar 14 is removably coupled with the catheter 20 (see, FIG. 7). As shown in FIG. 7, the catheter 20 generally comprises an annular proximal base 44 with diametrically opposed connection tabs 46 for threaded connection to the collar 14, an elongated barrel 48, and an elongated injection lumen 50 secured to the distal end of the barrel 48. Embodiments of the invention may also be used with other catheter designs, as well as other components permanently or removably secured to the injection site 10.

As also shown in FIG. 7, the cannula 18 or needle may be inserted into the split septum assembly 16 at the proximal end 26 of the injection site 10. The cannula 18 comprises a proximal annular base 52 and an externally ribbed barrel 54 terminating in an elongated injection lumen 56. The base 52 is provided with diametrically opposed connection tabs 58 configured for threaded connection with a standard luer lock fitting (not shown). In embodiments, the cannula 18 is a "blunt cannula" formed of a relatively rigid plastic or stainless steel and intended to provide needleless connection with a septum. Cannulas are commonly used with humans, whereas for animals, such as dogs and cats, it is more common to use a needle. As noted above, embodiments of the invention are for use with both cannulas and needles.

Turning now to FIGS. 3 and 7, the split septum assembly 16 of embodiments of the invention comprises a resilient and compressible split septum 60 having an axially-formed slit 62 for receipt of the blunt cannula 18, needle, or other medical device through said slit 62, a septum holder 64 for receipt of the split septum 60, and a septum housing 66 for receipt of the combined septum holder 64 and split septum 60. The septum 60, septum holder 64, and septum housing 66 are each independent and separated components, as opposed to being formed together. Moreover, the combined septum holder 64 and septum 60 is frictionally held within the septum housing 66, as described in more detail below, as opposed to be ultrasonically welded together. As noted above, the split septum assembly 16 is shown used with the luer body 12 that is a T-site body; however, the split septum assembly 16 may be used with other luer bodies.

The split septum 60 is formed of a synthetic isoprene with silica filler that in embodiments is free of natural rubber, latex, or mercaptobenzimidazol and has a hardness of 36-41 Shore A. As noted above, the split septum 60 is resilient and compressible. As more fully described below, the septum 60 is compressible along both an axial length and a transverse width. The septum 60 is also hermetically sealed within the injection site 10 to significantly minimize or completely prevent the expulsion of fluids out of the slit 62 in the septum 60, such as may occur upon removal of the cannula 18 or needle. The septum 60 is formed as a single, monolithic unit. The "pre-use position," as referenced herein, is the position of the septum 60 located in the septum holder 64, and the combined septum 60 and septum holder 64 located in the septum housing 66, as described below. In the pre-use position, the septum 60 is under compression due to being located in the septum holder 64 and septum housing 66, but the septum is not "in use" because the cannula 18, needle, or other medical device is not inserted in the septum 60. Thus, the "in use" position is when the cannula 18, needle, or other medical device is inserted into the septum 60. In contrast, a "rest" or "neutral" position is when the septum 60 is not located in the septum holder 64 or the septum housing 66, i.e., the septum 60 is not under compression.

Figure 8:
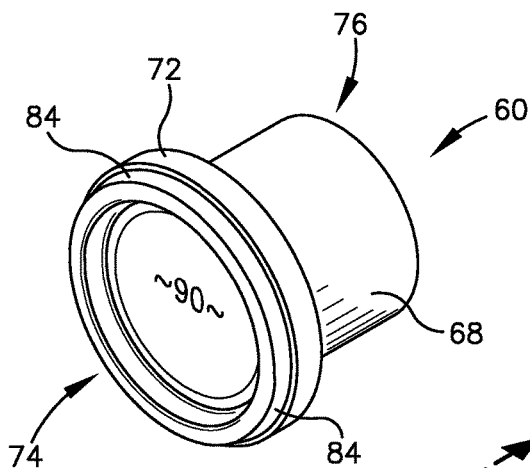
FIG. 8 is a distal perspective view of the septum of embodiments of the invention.
Figure 9:
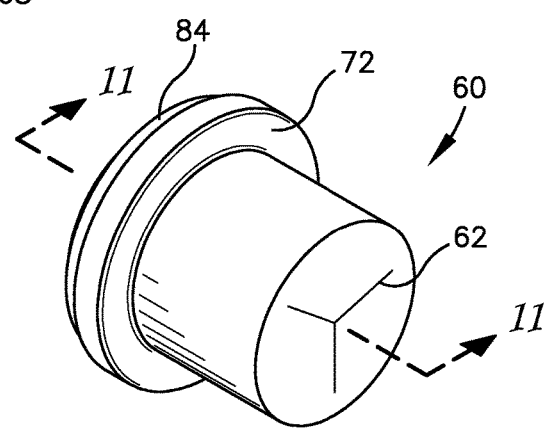
FIG. 9 is a proximal perspective view of the septum of FIG. 8.
Figure 10:
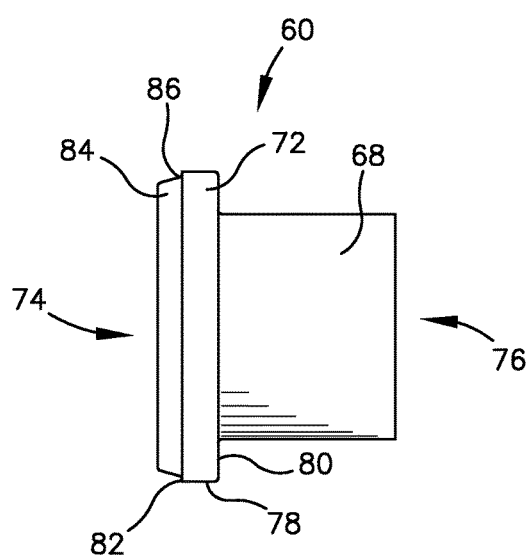
FIG. 10 is a side view of the septum of FIG. 8.

Referring to FIGS. 8-10, the split septum 60 includes a generally cylindrical body 68 presenting a radial-most outer surface 70 having an outer diameter, and an annular flange 72 circumscribing the radial-most outer surface 70 of the septum body 68 at a distal end 74 of the septum body 68. A proximal end 76 of the septum body 68 is numbered in FIGS. 8-10 for orientation purposes and ease of reference. Each of the cylindrical body 68 and the flange 72 has an axial length (i.e., the length along an axis of the fluid passageway 22 when the septum 60 is located in the luer body 12), and the axial length of the septum body 68 is greater than the axial length of the flange 72. In embodiments, the axial length of the septum body 68 is at least three times, five times, or ten times greater than the axial length of the flange 72. Transverse widths of the septum body 68 and the flange 72 are described below.

The slit 62 is formed in the septum 60 and extends along the entire axial length of the septum body 68. In embodiments, a plurality of slits 62 (see, e.g., FIG. 9) may be formed in the septum 60. For example, two slits 62 may be formed in the septum 60, and in embodiments, the slits 62 may be at generally ninety degrees to each other or at another angle. In yet further embodiments, three or more slits 62 may be formed in the septum 60, such as tri-slit formed in a Y-shape as illustrated in FIG. 9. When the septum 60 is in the pre-use or rest positions, the slit 62 is in a closed position, i.e., fluid does not flow through the slit 62. When the septum 60 is in the use position, the cannula 18, needle, or other medical device inserted into the slit 62 provides fluids that flow through the slit 62 and into the fluid passageway 22 of the injection site 10.

As illustrated in FIGS. 8-12, the flange 72 extends radially from the septum body 68 to present a radial-most outer edge 78 of the flange 72 having an outer diameter of the flange 72, and this outer diameter of the flange 72 is greater than the outer diameter of the septum body 68. Thus, the flange 72 projects radially further along a transverse axis than the septum body 68. In embodiments, the flange 72 is located at the distal end 74 of the septum body 68, and in other embodiments, the flange is located at a distal-most end of the septum body 68, wherein the distal-most end of the septum body 68 is the terminal end presenting a distal terminus of the body.

As best illustrated in FIGS. 11-12, the flange 72 presents a proximal-most surface 80 and a distal-most surface 82, wherein each of the proximal-most and distal-most surfaces 80,82 has a transverse width to present respective proximal-most and distal-most transverse surfaces (also identified as reference numerals 80,82, respectively). An annular locating and sealing projection 84 is formed on the distal-most transverse surface 82 and extends distally from the surface 82. The annular locating and sealing projection 84 is endless in that it extends around the entire annular flange 72. In alternative embodiments, a plurality of locating projections (not shown) may be formed on the distal-most transverse surface 82 of the flange 72 and extend distally from the surface 72, as opposed to the single annular projection illustrated in the Figures.

Referring to FIG. 12, the projection 84 (whether in the embodiment of the single annular projection or the embodiment of the plurality of projections) has a radial-most outer edge 86. In the annular projection embodiment illustrated in FIG. 12, the radial-most outer edge 86 presents an outer diameter, and this outer diameter is less than the outer diameter of the flange 72, which, as noted above, is presented at the radial-most outer edge 78 of the flange 72. The difference in the radial lengths between the radial-most outer edge 78 of the flange 72 and the radial-most outer edge 86 of the projection 84 creates a shelf 88 defined by the transition from the radial-most outer edge 78 of the flange 72 to the radial-most outer edge 86 of the projection 84. In the plurality of projections embodiment, a length from a center point of the septum 60 to the radial-most outer edge 78 of the flange 72 is larger than a length from the center point of the septum 60 to a radial-most outer edge of each projection to create a shelf defined by the transition from the radial-most outer edge 78 of the flange 72 to the radial-most outer edge of each projection. The purpose of the shelf 88 will be discussed in more detail below.

The locating and sealing projection of both embodiments is frustoconically shaped when viewed in vertical cross section, as shown in FIG. 12. Alternatively, the locating and sealing projection may be arcuate-shaped, such as hemispherical-shaped, or may be rectangular- or square-shaped when viewed in vertical cross section.

Figure 16:
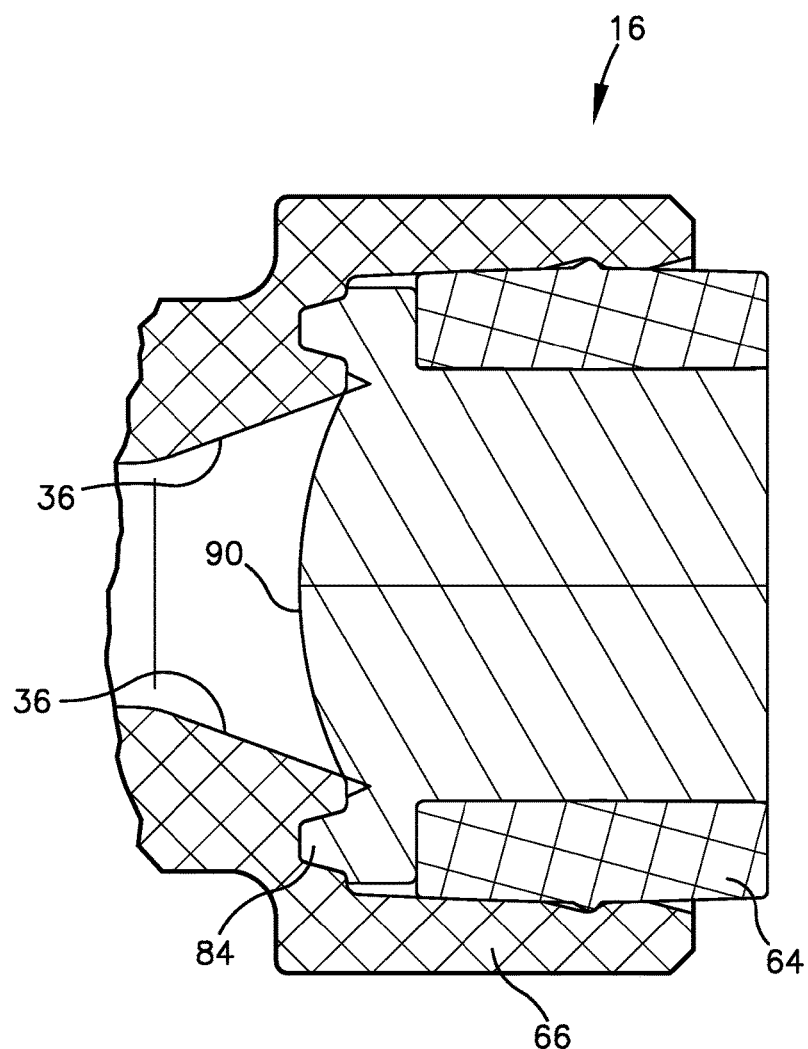
FIG. 16 is fragmentary, vertical cross-sectional view of a split septum assembly of embodiments of the invention and particularly illustrating a convex distal-most transverse surface of a septum body.

Referring to FIGS. 4 and 11, a distal-most transverse surface 90 of the septum body 68 is generally arcuate relative to the fluid passageway 22 of the injection site 10. That is, the distal-most transverse surface 90 of the septum body 68 is not substantially flat. In yet further embodiments and as shown in FIG. 4, the distal-most transverse surface 90 of the septum body 68 is concave relative to the fluid passageway 22 of the injection site 10, as illustrated in FIG. 4. In even yet further embodiments, the distal-most transverse surface 90 of the septum body 68 is convex relative to the fluid passageway 22 of the injection site 10, as illustrated in FIG. 16, such that at least a portion or all of the surface 90 extends distally past the distal-most surface 82 of the flange 72 when viewed in vertical cross-section. A convex distal-most transverse surface 90 of the septum body 68 presents the advantage of a longer axial length of the slit 62. Although the septum body 68 is described and illustrated as generally cylindrical, such that the distal-most transverse surface 90 of the septum body 68 is also cylindrical when viewed at either the distal or proximal ends 74 of the body 68, the distal-most transverse surface 90 of the septum body 68 may also be other shapes, such as elliptical, oval, horizontal, square, rectangular, or generally arcuate in horizontal cross-section.

Referring to FIGS. 11 and 12, a radial-most outer edge 92 of the distal-most transverse surface 90 of the septum body 68 lies in a transverse plane with the shelf 88 (hereinafter referred to as "the first shelf") created by the transition from the radial-most outer edge 78 of the flange 72 to the radial-most outer edge 86 of the locating and sealing projection 84. A second shelf 94 is created by the transition from a radial inner edge 96 of the projection 84 to the radial-most outer edge 92 of the transverse surface 90. The radial inner edge 96 of the projection 84 is, in embodiments, a radial-least inner edge, i.e., the inner edge portion of the projection 84 presenting the least distance from a center point of the septum 60 to the inner edge of the projection 84. This is due to the projection 84 having a frustoconical shape, such that there is a plurality of radii lengths from the center point of the septum 60 to the inner edge 96 of the projection 84. The first and second shelves 88,84 lie in the same transverse plane due to the projection 84 being integrally formed with the distal-most transverse surface 90 of the flange 72.

Figure 5:
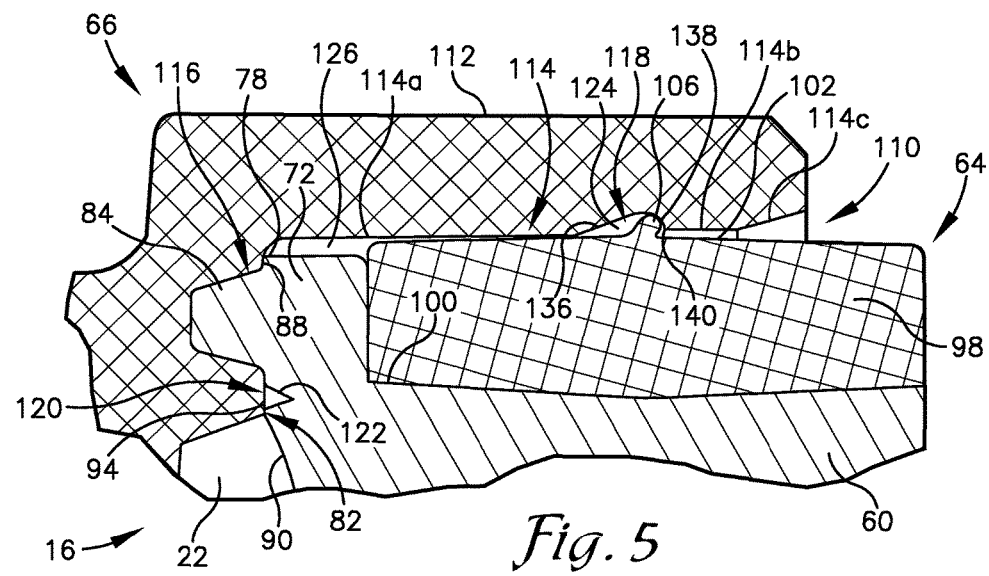
FIG. 5 is a magnified view of a portion of the injection site as indicated in detail 5 of FIG. 4.

Turning now to the septum holder 64 and FIGS. 13-15, the septum holder 64 is configured to receive the resilient and compressible split septum 60. The septum holder 64 is substantially rigid and has a generally cylindrically shaped body 98 presenting a radial-most outer surface 100 having an outer diameter and a radial-most inner surface 102 having an inner diameter. Due to its cylindrical shape, the septum holder 64 presents an open well 104 in which the septum body 68 is located. In embodiments of the invention, at least 50%, at least 80%, at least 90%, at least 95%, or 100% of the septum body 68 is located within the open well 104 of the septum holder 64. Thus, when the septum body 68 is positioned within the septum holder 64, the flange 72 of the septum 60 extends beyond the radial-most inner surface 102 of the septum holder body 98, as best illustrated in FIG. 5. Additionally, the axial length of the septum body 68 is at least 50%, at least 80%, at least 90%, at least 95%, or is the same as an axial length of the septum holder 64.

As illustrated in FIGS. 5 and 13-15, the septum holder 64 further includes an annular locking ring 106 formed on the radial-most outer surface 100 of the septum holder body 98 and circumscribing the body. The annular locking ring 106 is endless in that it extends around the entire cylindrically-shaped septum holder body 98. In alternative embodiments, a plurality of locking projections (not shown) may be formed on the outer surface 100 of the body 98.

The locking ring 106 is deformable in either or both of a transverse and axial direction. As described below, this is advantageous when inserting the septum holder 64 within the septum housing 66. Because the locking ring 106 is deformable, it has a pre-use shape that is generally symmetrical about a transverse axis and an in-use shape that is generally asymmetrical. The pre-use locking ring 106 is shown in FIGS. 14-15. As illustrated, the locking ring 106 is substantially hemispherical in horizontal cross section, although other symmetrical shapes could be used. In embodiments, the pre-use shape of the locking ring 106 is also arcuate when viewed in horizontal cross section. In alternative embodiments, the pre-use shape of the locking ring 106 may be generally frustoconical, rectangular, or square shaped.

The in-use locking ring 106 is shown in FIG. 5. In embodiments, the locking ring 106 is angled towards the proximal end 26 of the injection site 10 when the septum holder 64 is mounted within the septum housing 66. Thus, the locking ring 106 is not symmetrical about a transverse axis of the septum holder 64 when in-use. As discussed below, when in-use, the locking ring 106 illustrated in FIGS. 5 and 15 presents a bulbous end.

The locking ring 106 is located at a substantial mid-point of an axial length of the septum holder 64, as best illustrated in FIG. 14, such that the locking ring 106 generally bisects the axial length of the holder 64. In embodiments where the locking ring 106 is substantially symmetrical, the split septum 60 may be positioned within the septum holder 64 by locating the septum body 68 through either of a proximal or a distal end of the septum holder 64. Alternatively stated, the septum holder 64 allows bi-directional insertion of the septum 60 into the septum holder 64, such that the septum 60 can be located in the septum holder 64 from either axial direction of the septum holder 64.

When the septum holder 64 is viewed in plan, i.e., viewed from a proximal-up orientation or a distal-down orientation, it can be seen that the locking ring 106 presents a radial-most outer surface 108 that has an outer diameter, and this outer diameter is larger than the outer diameter of the radial-most outer surface 100 of the septum holder body 98. Thus, the locking ring 106 extends transversely from the septum holder body 98.

The septum 60 is frictionally held within the septum holder 64. In some embodiments, the radial-most outer diameter of the septum body 68 is slightly larger than the radial-most inner diameter of the septum holder 64, but in other embodiments the radial-most outer diameter of the septum body 68 is substantially the same as the radial-most inner diameter of the septum holder 64. In either embodiment, the friction between the resilient material of the septum body 68 and the septum holder 64 is sufficient to preassemble the septum 60 in the septum holder 64 prior to being assembled in the septum housing 66. As discussed in more detail below, upon insertion of the combined septum 60 and septum holder 64 in the septum housing 66, the septum 60 undergoes a transverse compression.

Turning to FIGS. 3-5, the septum housing 66 will now be described. In embodiments of the invention, the septum housing 66 is integrally formed with the luer body 12 and extends from the proximal end of the luer body 12, such that the luer body 12 is a monolithic structure with the septum housing 66. In alternative embodiments, the septum housing 66 is a separate unit from the luer body 12 and is coupled to the luer body 12 to provide the fluid passageway 22 through the injection site 10.

Figure 2:
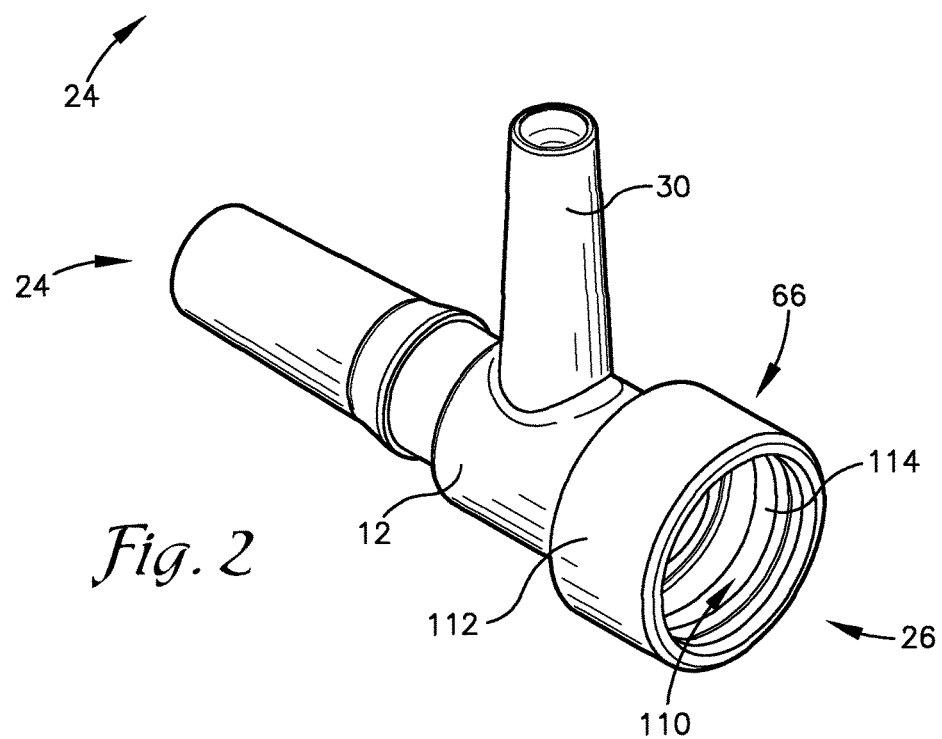
FIG. 2 is a second perspective view of the injection site of FIG. 1.

As illustrated in FIG. 2, the septum housing 66 presents a general cup-like opening 110 (hereinafter the "cup") for receipt of the combined septum holder 64 and the septum 60. Thus, the septum 60 is first positioned in the septum holder 64, and then the combined septum holder 64 and the septum 60 are positioned in the cup 110 of the septum housing 66. The cup 110 is generally cylindrically-shaped, such that a proximal end receives the combined septum holder 64 and the septum 60, and a distal end is fluidly connected to the fluid passageway 22 of the injection site 10. Because the septum housing 66 extends proximally from the distal end of the luer body 12, the angled fluid passageway walls 36 intersect the septum 60, and specifically the distal-most transverse surface 90 of the septum 60, held in the septum housing 66, as best illustrated in FIG. 4.

Referring to FIGS. 2 and 5, the cup 110 of the septum housing 66 presents a radial-most outer wall 112 (i.e., the external or outer wall of the cup 110 of the septum housing 66) and a radial-most inner wall 114 (i.e., the interior or inner wall of the cup 110 of the septum housing 66). An annular locating groove 116 is formed in a distal transverse surface 120 of the septum housing 66 for receipt of the annular locating and sealing projection 84 formed on the distal-most surface 82 of the flange 72, as further described below. Additionally, an annular locking groove 118 is formed on the radial-most inner wall 114 of the cup 110 for receipt of the locking ring 106 formed on the septum holder body 98, as also described below.

The radial-most outer wall 112 of the cup 110 presents an outer diameter of the septum housing 66, and the outer diameter of the septum housing 66 is substantially the same along an entire axial length of the septum housing 66. In contrast, the radial-most inner wall 114 of the cup 110 presents a plurality of inner wall segments 114a, 114b, 114c corresponding to different inner diameters, as best illustrated in FIG. 5. The inner diameter of the inner wall 114 is smallest at the distal-most end of the septum housing 66, where the inner wall 114 gradually angles outwardly as the proximal end of the septum housing 66 is approached for an axial length corresponding to a first inner wall segment 114a. An innermost portion of the first inner wall segment 114a, which is located at approximately the radial-most outer edge 78 of the flange 72, has an inner diameter smaller than an innermost portion of a second inner wall segment 114b. The purpose for the first inner wall segment 114a to be angled is discussed further below. The inner wall 114 transitions from the first inner wall segment 114a to the locking groove 118 at a proximal-most end of the first inner wall segment 114a. The locking groove 118 is also discussed in more detail below. The inner wall 114 then transitions from the locking groove 118 to the second inner wall segment 114b, which is generally axially straight. Finally, the inner wall 114 transitions from the second inner wall segment 114 to a third inner wall segment 114c at a proximal-most end of the second inner wall segment 114b. The third inner wall segment 114c is sharply angled outwardly as the proximal end of the septum housing 66 is approached. The angle of the third inner wall segment 114c, relative to the straight second inner wall segment 114b is approximately 5-20 degrees, approximately 10-15 degrees, or approximately 12.6 degrees.

Turning to FIGS. 4-5 and the annular locating groove 116 for receipt of the projection 84 on the flange 72, the groove 116 is substantially complementary shaped with the shape of the projection 84. Thus, in embodiments where the projection 84 is frustconically shaped, the locating groove 116 is also frustoconically shaped to receive the projection 84. An axial length of the annular projection 84 when positioned in the locating groove 116 is approximately 0.5 mm. As discussed above, in some embodiments, the projection may not be annular but instead may comprise the plurality of projections. In such an embodiment, the annular locating groove may also not be annular and instead comprising a series of complementary-shaped openings for receipt of the respective plurality of projections. As also noted above, the annular locating groove 116 is formed in the distal transverse surface 120 of the septum housing 66. Thus, the distal transverse surface 120 of the septum housing 66 juts slightly inwardly towards the fluid passageway 22 to receive the projection 84 on the flange 72.

Recall the first shelf 88 of the flange 72 is defined by the transition from the radial-most outer edge 78 of the flange 72 to the radial-most outer edge 86 of the locating and sealing projection 84. Additionally, the second shelf 94 of the flange 72 is created by the transition from the radial inner edge 96 of the projection 84 to the radial-most outer edge 92 of the transverse surface 90 of the septum body 68. When the combined septum holder 64 and septum 60 are mounted within the septum housing 66, the first and second shelves 88,94 rest against the distal transverse surface 120 of the septum housing 66.

As illustrated in FIGS. 4-5, a barb 122 projects proximally from the distal transverse surface 120 of the septum housing 66 to assist in grasping the septum 60 when the septum 60 is positioned in the septum housing 66. The barb 122 is generally angled in a reverse V-shape, such that the barb 122 is pointed at its proximal end to push into the resilient and compressible material of the septum 60. Upon the septum 60 being positioned within the septum housing 66, the barb 122 will press into a portion of the second shelf 94 of the septum 60, which was described above.

Referring to FIG. 5, the annular locking groove 118 formed on the inner wall 114 of the cup 110 will be described in more detail. The locking groove 118 is generally arcuate along its axial length when viewed in cross section, as shown in FIG. 5. The locking groove 118 comprises an axial wall 136 and transverse wall 138. The transverse wall 138 extends generally radially outwardly, and the axial wall 136 extends generally axially. The axial wall 136 curves into the transverse wall 138 to form a continuous, arcuate groove. The transverse wall 138 includes an inner edge 140 (which is the proximal-most end of the groove 118) that must be overcome for the locking ring 106 to snap-fit into the locking groove 118.

The distal-most end of the axial wall 136 intersects the proximal-most edge of the first inner wall segment 114a. As the proximal end of the axial wall 136 is approached, the axial wall 136 tapers radially outwardly. At approximately the axial wall's radially-most outward end, the axial wall 136 transitions to the transverse wall 138 as the proximal end of the locking groove 118 is approached. The transverse wall 138 then curves radially inwardly to intersect the distal-most edge of the second inner wall segment 114b. The locking groove 118 thus forms the general shape of half of a heart, as illustrated in FIG. 5. However, it should be appreciated that the locking groove 118 may be other shapes.

The locking groove 118 is, in embodiments of the invention, not complementary shaped to either of the pre-use or in-use shapes of the locking ring 106 transversely extending from and formed on the septum holder body 98. Instead, the locking groove 118 provides a depression that is shaped to allow the locking ring 106 to slide into the locking groove 118, deform, and snap-fit into a locked position. More particularly, when the locking ring 106 is in place within the locking groove 118, an area 124 of the locking groove 118 distal of the locking ring 106 is open (i.e., not filled with the locking ring 106), and this open area 124 is more than any open area of the locking groove 118 proximal of the locking ring 106. When the locking ring 106 is snap-fit into the locking groove 118, a bulbous end of the locking ring 106 is located at the proximal end of the locking groove 118. In particular, when the locking ring 106 overcomes the proximal-most edge of the locking groove 118, the locking ring 106 deforms proximally (i.e., it is manipulated by the interaction with the locking groove 118 to be deformed proximally), such that the locking ring 106 forms the bulbous end that presses against the transverse wall 138 of the locking groove 118. Because the locking ring 106 is, in embodiments, deformable in either or both of a transverse or axial direction, this allows sufficient movement or "give" of the bulbous end of the locking ring 106 to deform into position within the locking groove 118.

As noted above, the third inner wall segment 114c of the septum housing 66 is angled sharply outwardly as the proximal end of the septum housing 66 is approached. The sharp angle facilitates locating the septum holder 64 in the septum housing 66. In particular and as noted above, the locking ring 106 on the septum holder 64 is snap-fit into position within the locking groove 118. During positioning of the septum holder 64 in the septum housing 66, the locking ring 106 slides against the angled third inner wall segment 114c, which slightly compresses the septum holder 64 inwardly along a transverse axis. Upon the locking ring 106 being received in the locking groove 118, the septum holder 64 retracts axially outward. However, due to the first inner wall segment 114a having an inner diameter that is the smallest along the entire axial length of the septum housing inner wall 114, a distal segment of the septum holder 64, i.e., the segment of the septum holder 66 extending generally distally from the locking ring 106, is compressed radially inwardly along the transverse axis. Although the radial inward compression of the septum holder 66 is relatively small, e.g., approximately 0.1 mm, this compression in turn translates to the septum 60 located in the septum holder 66 to also compress the septum 60 radially inwardly along the transverse axis. Thus, the components of the split septum assembly 16 of embodiments of the invention collectively work together to compress the septum 60 radially inwardly along a transverse axis and at the distal end 74 of the septum body 68.

As also illustrated in FIGS. 4-5, the outer diameter of the radial-most outer edge 78 of the flange 72 is less than the radial-most inner diameter of the septum holder 64 to present a gap 126 between the radial-most outer edge 78 of the flange 72 and the first inner wall segment 114a of the septum housing 66. The gap 126 provides an open area in which the septum flange 72 may expand radially upon insertion of the cannula 18, needle, etc. As can be appreciated, a volume of the septum 60 is displaced upon insertion of the cannula 18, and this displaced volume of the septum 60 must be able to expand into an open area. Often in prior art devices, the expansion occurs along the proximal or distal transverse surfaces of the septum 60. In embodiments of the invention, the distal-most transverse surface 90 of the septum body 68 does not experience any distal displacement upon insertion of the cannula 18, needle, etc. That is, when the cannula 18 is inserted into the septum 60, the distal-most transverse surface 90 does not expand or otherwise move into the fluid passageway 22. Thus, the location of the distal-most transverse surface 90 of the septum 60 in a rest state is in the same position as an in use state when the cannula 18 is inserted into the septum 60. However, when the cannula 18 is inserted into the septum 60, a proximal-most transverse surface of the septum body 68 is displaced proximally beyond a proximal-most horizontal plane of the septum holder 64.

Positioning of the combined septum holder 64 and septum 60 in the septum housing 66 also axially compresses the flange 72 of the septum 60 to present a double hermetic seal. In particular and as illustrated in FIG. 5, the flange 72 compresses axially in a distal direction approximately 0.1 mm from its rest position when held within the septum holder 64, to its pre-use position when the combined septum holder 64 and septum 60 are positioned in the septum housing 66. A first hermetic seal is formed at and around the second shelf 94, such that fluid from the fluid passageway 22 does not leak between the distal-most surface 82 of the flange 72 and the distal transverse surface 120 of the septum housing 66. However, in the event that any fluid does leak into the locating groove 116 for the projection 84, a second hermetic seal is formed at the first shelf 88 to prevent fluid from leaking into the gap 126 between the radial-most outer edge 78 of the flange 72 and the septum holder 64. Thus, the septum 60 is hermetically sealed within the injection site 10 to minimize or completely prevent the proximal expulsion of fluids out of the slit 62 in the septum 60 or around the septum holder 64, such as may occur upon removal of the cannula 18 or needle. Additionally, the receipt of the projection 84 within the locating groove 116 serves to prevent entrapment of fluids underneath the projection 84 and the flange 72.

Figure 6:
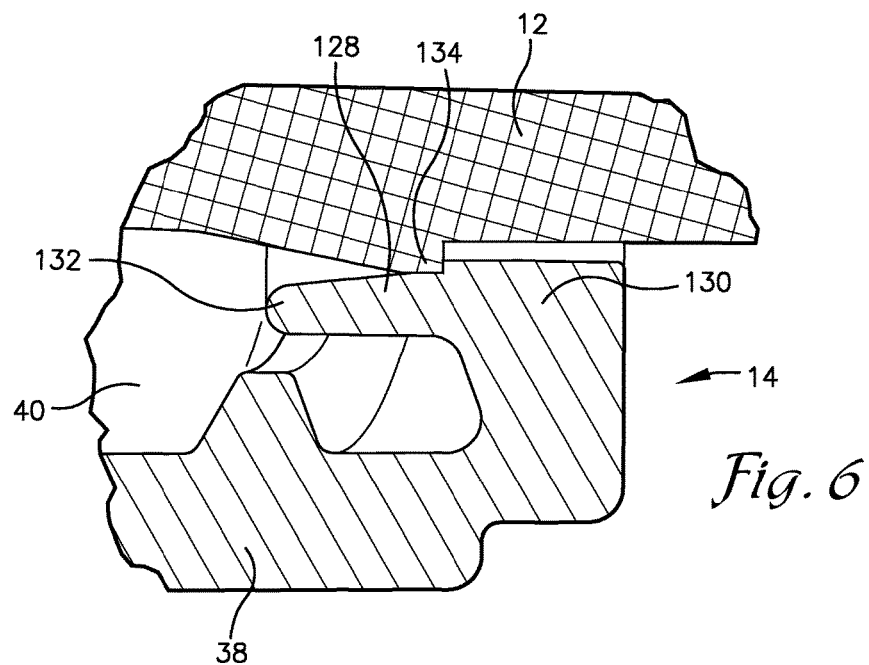
FIG. 6 is a magnified view of a portion of the injection site as indicated in detail 6 of FIG. 4.

Turning to FIGS. 4 and 6, anti-rotation features of the rotating threaded collar 14 will now be discussed. The threaded rotating collar 14 includes an annular anti-rotation ring 128 extending annularly around a proximal end of the rotating collar 14. The anti-rotation ring 128 is formed on a distal facing transverse surface 130 of the collar 14 and extends distally from the surface 130. The ring 128 is slightly tapered as it extends distally to its terminus 132. The ring 128 acts as a stop as the plurality of threads 40 of the collar 14 are rotated about the luer body 12. Thus, as the proximal-most thread 40 of the rotating threaded collar 14 comes into contact with the anti-rotation ring 128, the ring 128 prevents the threaded collar 14 from rotating proximally further. Additionally, the ring 128 provides enough frictional stoppage to require a relatively large initial force to reverse rotation of the threaded collar 14 to remove the collar 14 from the luer body 12. In embodiments of the invention, the anti-rotation ring 128 operates in conjunction with an inwardly transversely extending barb 134 that also extends proximally upwards from the luer body 12. The barb 134 serves to catch the anti-rotation ring 128 and provide frictional resistance to prevent further rotation of the collar 14 or prevent rotation in a reverse direction.

Although the invention has been described with reference to the embodiments illustrated in the attached drawing figures, it is noted that equivalents may be employed and substitutions made herein without departing from the scope of the invention as recited in the claims. For example, instead of forming the projection 84 on the flange 72, the projection 84 could be formed on the transverse distal surface 120 of the septum housing 66. In this embodiment, the locating groove 116 would then be formed on the proximal transverse surface of the flange 72. Similarly, instead of the locking ring 106 being formed on the septum holder body 98, the locking ring 106 could be formed on the inner surface 102 of the septum housing 66, such that the locking ring 106 extends radially inwardly. The locking groove 118 would then be formed on the outer wall of the septum holder 64.

Having thus described various embodiments of the invention, what is claimed as new and desired to be protected by Letters Patent includes the following:

1. A split septum assembly for coupling with a miniaturized intravenous injection site used to administer fluids to a patient, the split septum assembly presenting an axial length extending along an axis of a fluid passageway of the intravenous injection site when the split septum assembly is coupled with the site, a transverse width, a distal end oriented towards a patient when the split septum assembly is coupled with the intravenous injection site, and a proximal end oriented towards a clinician administering fluids to the patient, the split septum assembly comprising:
 a resilient and compressible split septum having an axially-formed slit for receipt of a blunt cannula, needle, or other medical device through said slit,
 said septum including a generally cylindrical body presenting a radial-most outer surface that has an outer diameter, and an annular flange circumscribing the radial-most outer surface of the septum body at a distal end of the septum body,
 wherein an axial length of the septum body is greater than an axial length of the flange,
 said flange extending radially from the septum body to present a radial-most outer edge of the flange having an outer diameter of the flange,
 wherein said outer diameter of the flange is greater than the outer diameter of the septum body,
 said flange including a proximally-extending locating projection annularly formed on the flange;
 a septum holder for receipt of the split septum, said septum holder having a generally cylindrically shaped body presenting a radial-most outer surface having an outer diameter and a radial-most inner surface having an inner diameter,
 said septum holder including an annular locking ring formed on the radial-most outer surface of the septum holder body and circumscribing the septum holder body,
 wherein a shape of the locking ring in a pre-use position of the intravenous injection site is symmetrical in cross section, and a shape of the locking ring in an in-use position of the intravenous injection site is asymmetrical in cross section,
 wherein said split septum body is configured to be positioned within the septum holder, such that the split septum flange extends beyond a transverse periphery of the septum holder; and
 a septum housing for receipt of the combined septum holder and split septum, the septum housing having a proximal end that is open for positioning of the combined septum holder and split septum therethrough, and a distal end that is open to the fluid passageway of the injection site,
 said septum housing having a generally cylindrically shaped body having a radial-most outer surface and a radial-most inner surface presenting an inner diameter, a proximally-extending annular locating groove for receipt of the locating projection, and a radially-extending annular locking groove for interconnecting with the locking ring formed on the septum holder.

2. The split septum assembly of claim 1, wherein the septum holder is generally rigid for receipt of the resilient and compressible split septum.

3. The split septum assembly of claim 1, wherein an outer diameter of the locating projection is less than the outer diameter of the flange.

4. The split septum assembly of claim 1, wherein the locating projection on the flange has a shape when viewed in vertical cross section selected from the group consisting of a frustoconical shape and a hemispherical shape.

5. The split septum assembly of claim 1,
wherein the flange circumscribes the outer diameter of the septum body at a distal-most edge of the body,
wherein a radial-most outer edge of the flange is the outer diameter,
wherein the flange presents a proximal-most transverse surface and a distal-most transverse surface,
wherein the locating projection on the flange extends from the distal-most transverse surface,
wherein a radial-most outer edge of the locating projection has a diameter less than the outer diameter of the flange, such that a transition from the radial-most outer edge of the flange to the radial-most outer edge of the locating projection presents a shelf.

6. The split septum assembly of claim 5, wherein a proximal-most transverse surface of the septum body is one of concave or convex relative to the fluid passageway of the injection site.

7. The split septum assembly of claim 6, wherein the one of the concave or convex surface of the septum body is generally circular when viewed from the distal end of the septum, and a radial-most outer edge of the concave surface lies in a transverse plane with the shelf.

8. The split septum assembly of claim 1, wherein a distal-most transverse surface of the septum body is generally arcuate relative to the fluid passage of the injection site.

9. The split septum assembly of claim 1, wherein the locking ring is deformable in either or both of a transverse or an axial direction, such that the locking ring may be snap-fit into the locking groove, and upon being snap-fit, the locking ring presents a bulbous end.

10. The split septum assembly of claim 9,
wherein the locking groove includes an axial wall that tapers radially outwardly as the proximal end of the injection site is approached, and a transverse wall that extends radially outwardly,
wherein the locking ring is deformed proximally upon being snap-fit into the locking groove, such that the locking ring presses against the transverse wall,
wherein the locking ring, upon being snap-fit into the locking groove, does not fill an entire open area of the locking groove,
wherein an area of the locking groove distal of the locking ring is open and not filled with the locking ring when the locking ring is snap-fit into the locking groove.

11. The split septum assembly of claim 1, wherein upon insertion of a combined septum and septum holder in the septum housing, a distal end of the septum holder is compressed transversely to compress the septum.

12. The split septum assembly of claim 1, wherein the axial length of the septum body is substantially the same as an axial length of the septum holder.

13. The split septum assembly of claim 1, wherein the outer diameter of the radial-most outer edge of the flange is less than the radial-most inner diameter of the septum holder to present a gap between the radial-most outer edge of the flange and the radial-most inner diameter of the septum housing.

14. The split septum assembly of claim 1, wherein the septum housing is integrally formed with a body of the intravenous injection site.

15. The split septum assembly of claim 1, wherein the septum housing further includes a proximal-projecting barb for grasping the split septum when the septum is positioned in the septum housing.

16. The split septum assembly of claim 1,
wherein the septum housing has a radial-most annular inner wall, and the annular inner wall has at least two different inner diameters along its axial length,
wherein the radial-most annular inner wall of the septum housing is comprised of three inner wall segments presenting at least three different inner diameters along the axial length of the inner wall,
wherein a first inner wall segment is angled outwardly as the proximal end of the injection site is approached,
wherein a second inner wall segment is generally axially straight to present a single diameter along the axial length of the second inner wall segment,
wherein a third inner wall segment is angled sharply outwardly as the proximal end of the injection site is approached for receipt of the locking ring.

17. A split septum assembly for coupling with a miniaturized intravenous injection site used to administer fluids to a patient, the split septum assembly presenting an axial length extending along an axis of a fluid passageway of the intravenous injection site when the split septum assembly is coupled with the site, a transverse width, a distal end oriented towards a patient when the split septum assembly is coupled with the intravenous injection site, and a proximal end oriented towards a clinician administering fluids to the patient, the split septum assembly comprising:
a resilient and compressible split septum having an axially-formed slit for receipt of a blunt cannula, needle, or other medical device through said slit,
said septum including a generally cylindrical body presenting a radial-most outer surface that has an outer diameter, and an annular flange circumscribing the radial-most outer surface of the septum body at a distal end of the septum body,
wherein an axial length of the septum body is greater than an axial length of the flange,
said flange extending radially from the septum body to present a radial-most outer edge of the flange having an outer diameter of the flange,
wherein said outer diameter of the flange is greater than the outer diameter of the septum body,
said flange including a proximally-extending locating projection annularly formed on the flange;
a septum holder for receipt of the split septum, said septum holder having a generally cylindrically shaped body presenting a radial-most outer surface having an outer diameter and a radial-most inner surface having an inner diameter,
said septum holder including an annular locking ring formed on the radial-most outer surface of the septum holder body at a substantial mid-point of an axial length of the septum holder and circumscribing the septum holder body, wherein the locking ring presents a radial-most outer surface that has an outer diameter that is larger than the outer diameter of the radial-most outer surface of the septum holder body, wherein a shape of the locking ring in a pre-use position of the intravenous injection site is symmetrical in cross section, and a shape of the locking ring in an in-use position of the intravenous injection site is asymmetrical in cross section, wherein said split septum body is configured to be positioned within the septum holder, such that the split septum flange extends beyond a transverse periphery of the septum holder; and a septum housing for receipt of the combined septum holder and split septum, the septum housing having a proximal end that is open for positioning of the combined septum holder and split septum therethrough, and a distal end that is open to the fluid passageway of the injection site, said septum housing having a generally cylindrically shaped body having a radial-most outer surface and a radial-most inner surface presenting an inner diameter, a proximally-extending annular locating groove for receipt of the locating projection, and a radially-extending annular locking groove for interconnecting with the locking ring formed on the septum holder.

18. The split septum assembly of claim 1, wherein the flange circumscribes the outer diameter of the septum body at a distal-most edge of the body, wherein a radial-most outer edge of the flange is the outer diameter, wherein the flange presents a proximal-most transverse surface and a distal-most transverse surface, wherein the locating projection on the flange extends from the distal-most transverse surface, wherein a radial-most outer edge of the locating projection has a diameter less than the outer diameter of the flange, such that a transition from the radial-most outer edge of the flange to the radial-most outer edge of the locating projection presents a shelf.

19. The split septum assembly of claim 17, wherein a proximal-most transverse surface of the septum body is one of concave or convex relative to the fluid passageway of the injection site, wherein the one of the concave or convex surface of the septum is generally circular when viewed from the distal end of the septum, and a radial-most outer edge of the concave surface lies in a transverse plane with the shelf.

20. The split septum assembly of claim 17, wherein the locking ring is deformable in either or both of a transverse or an axial direction, such that the locking ring may be snap-fit into the locking groove, and upon being snap-fit, the locking ring presents a bulbous end, wherein the locking groove includes an axial wall that tapers radially outwardly as the proximal end of the injection site is approached, and a transverse wall that extends radially outwardly, wherein the locking ring is deformed proximally upon being snap-fit into the locking groove, such that the locking ring presses against the transverse wall, wherein the locking ring, upon being snap-fit into the locking groove, does not fill an entire open area of the locking groove, wherein an area of the locking groove distal of the locking ring is open and not filled with the locking ring when the locking ring is snap-fit into the locking groove.

21. The split septum assembly of claim 17, wherein upon insertion of a combined septum and septum holder in the septum housing, a distal end of the septum holder is compressed transversely to compress the septum.

22. The split septum assembly of claim 17, wherein the septum housing has a radial-most annular inner wall, and the annular inner wall has at least two different inner diameters along its axial length, wherein the radial-most annular inner wall of the septum housing is comprised of three inner wall segments presenting at least three different inner diameters along the axial length of the inner wall, wherein a first inner wall segment is angled outwardly as the proximal end of the injection site is approached, wherein a second inner wall segment is generally axially straight to present a single diameter along the axial length of the second inner wall segment, wherein a third inner wall segment is angled sharply outwardly as the proximal end of the injection site is approached for receipt of the locking ring.

* * * * *